(12) United States Patent
Czibula et al.

(10) Patent No.: US 8,569,498 B2
(45) Date of Patent: Oct. 29, 2013

(54) PROCESS FOR THE PREPARATION OF PIPERAZINE COMPOUNDS AND HYDROCHLORIDE SALTS THEREOF

(75) Inventors: Laszlo Czibula, Budapest (HU); Balint Juhasz, Torokbalint (HU); Eva Againe Csongor, Pomaz (HU); Ferenc Sebok, Mezokovacshaza (HU); Janos Galambos, Budapest (HU); Katalin Nogradi, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 173 days.

(21) Appl. No.: 13/140,281

(22) PCT Filed: Dec. 18, 2009

(86) PCT No.: PCT/HU2009/000109
§ 371 (c)(1),
(2), (4) Date: Jul. 27, 2011

(87) PCT Pub. No.: WO2010/070370
PCT Pub. Date: Jun. 24, 2010

(65) Prior Publication Data
US 2011/0275804 A1 Nov. 10, 2011

(30) Foreign Application Priority Data

Dec. 18, 2008 (HU) .................................... 0800765

(51) Int. Cl.
*C07D 295/135* (2006.01)
*C07D 295/14* (2006.01)

(52) U.S. Cl.
USPC .......................................... 544/393; 544/121

(58) Field of Classification Search
None
See application file for complete search history.

(56) References Cited

U.S. PATENT DOCUMENTS

| 4,957,921 | A | 9/1990 | Caprathe et al. |
| 5,846,514 | A | 12/1998 | Foster et al. |
| 6,334,997 | B1 | 1/2002 | Foster et al. |
| 6,489,341 | B1 | 12/2002 | Jerussi |
| 6,528,529 | B1 | 3/2003 | Brann et al. |
| 6,566,550 | B2 | 5/2003 | Lowe, III |
| 6,919,342 | B2 | 7/2005 | Haupt |
| 7,122,576 | B2 | 10/2006 | Plata-Salaman et al. |
| 7,737,142 | B2 | 6/2010 | Csongor et al. |
| 7,829,569 | B2 | 11/2010 | Liao et al. |
| 7,875,610 | B2 | 1/2011 | Szalai et al. |
| 7,943,621 | B2 | 5/2011 | Czibula et al. |
| 7,981,897 | B2 | 7/2011 | Bathe et al. |
| 2003/0144285 | A1 | 7/2003 | Brann et al. |
| 2004/0259882 | A1 | 12/2004 | Haupt et al. |
| 2005/0107397 | A1 | 5/2005 | Galambos et al. |
| 2006/0229297 | A1 | 10/2006 | Csongor et al. |
| 2007/0259885 | A1 | 11/2007 | Bathe et al. |
| 2010/0137335 | A1 | 6/2010 | Csongor et al. |
| 2010/0197666 | A1 | 8/2010 | Laszlovsky et al. |
| 2010/0197704 | A1 | 8/2010 | Laszlovsky et al. |
| 2010/0256145 | A1 | 10/2010 | Bak-Jensen et al. |
| 2011/0059980 | A1 | 3/2011 | Oobayashi |
| 2011/0112093 | A1 | 5/2011 | Szalai et al. |
| 2011/0269959 | A1 | 11/2011 | Csongor et al. |
| 2011/0275816 | A1 | 11/2011 | Czibula et al. |

FOREIGN PATENT DOCUMENTS

| EP | 0431580 | 3/1995 |
| WO | WO 97/11070 | 3/1997 |
| WO | WO 99/50247 | 10/1999 |
| WO | WO 99/67206 | 12/1999 |
| WO | WO 01/05763 | 1/2001 |
| WO | WO 03/029233 | 4/2003 |
| WO | WO 03/064393 | 8/2003 |
| WO | WO 2005/012266 | 2/2005 |
| WO | WO 2006/082456 | 8/2006 |
| WO | WO 2007/033191 | 3/2007 |
| WO | WO 2008/139235 | 11/2008 |
| WO | WO 2008/141135 | 11/2008 |
| WO | WO 2008/142461 | 11/2008 |
| WO | WO 2010/009309 | 1/2010 |

OTHER PUBLICATIONS

EP Search Report dated Mar. 4, 2010, mailed Mar. 11, 2010, Authorized Officer Marc Gettins.

(Continued)

*Primary Examiner* — Emily Bernhardt
(74) *Attorney, Agent, or Firm* — Fish & Richardson P.C.

(57) ABSTRACT

The invention relates to a new process for the preparation of compounds of general formula (I) wherein
$R_1$ and $R_2$ represent independently hydrogen or
$C_{1-6}$ alkyl with straight or branched chain optionally substituted with aryl group, or
$C_{2-7}$ alkenyl containing 1-3 double bonds, or
monocyclic, bicyclic or tricyclic aryl optionally substituted with one or more C1-6 alkoxy, trifluoro-$C_{1-6}$ alkoxy, $C_{1-6}$-alkoxycarbonil, $C_{1-6}$alkanoyl, aryl, $C_{1-6}$ alkylthio, halogen or cyano, or
optionally substituted monocyclic, bicyclic or tricyclic $C_{3-14}$ cycloalkyl group,
$R_1$ and $R_2$ together with the adjacent nitrogen form a saturated or unsaturated optionally substituted monocyclic or bicyclic heterocyclic ring which may contain further heteroatoms selected from oxygen, nitrogen, or sulphur atoms and hydrochloric acid alts and/or hydrates and/or solvates thereof, by dissolving or suspending trans 4-{2-[4-(2,3-dichlorophenyl)-piperazine-1-il]-ethyl}-cyclohexylamine of formula (III) or a salt or a hydrate or a solvate thereof in an inert solvent in the presence a base then adding a carbonic acid derivative of general formula (VI) wherein R is alkyl with $C_{1-6}$ straight or branched chain or $C_{1-2}$ fully halogenated alkyl, Z is —O—R or —X, wherein R is as described above, X is halogen, and reacting the compound of general formula (IV) obtained wherein R is as described above, in situ or, optionally in isolated state with an amine of general formula (V) wherein $R_1$ and $R_2$ are as described above to obtain the compound of general formula (I) and then optionally forming the hydrochloride salts and/or hydrates and/or solvates thereof.

3 Claims, No Drawings

(56) References Cited

OTHER PUBLICATIONS

Han; Advances in Characterization of Pharmaceutical Hydrates; Trends in Bio/Pharmaceutical Industry; 2006; 2(3): 25-29.

Vippagunta et al; Crystalline Solids; Advanced Drug Delivery Reviews; 2001; 48(1):3-26.

Aiken, "Pramipexole in psychiatry: A systematic review of the literature," *J. Clin Psychiatry.*, 68(8):1230-1236, (2007).

Baldessarini and Tarazi, "Pharmacotherapy of Psychosis and Mania," Brunton et al. (eds.), *Goodman and Gilman's The Pharmacological Basis of Therapeutics*, 11th Edition, McGraw Hill, Chapter 18, pp. 462-500, (2005).

Belliotti, et al., "Novel cyclohexyl amides as potent and selective D3 dopamine receptor ligands," *Bioorganic & Medicinal Chemistry Letters*, 7(18):2403-2408, (1997).

Berge et al., "Pharmaceutical salts," *Journal of Pharmaceutical Sciences*, 66(1):1-19 (1977).

Bézard et al., "Attenuation of levodopa-induced dyskinesia by normalizing dopamine D3 receptor function," *Nat. Med.*, 9(6):762-767, (2003).

*Burger's Medicinal Chemistry and Drug Discovery.* vol. 1. Drug Discovery, 6th Edition Wiley Interscience. Ed. Donald J. Abraham, ISBN 978-0-471-27090-4, Jan. 2003.

Creese et al., "Species variation in dopamine receptor binding," *Eur. J. Pharmacol.*, 60:55-66, (1979).

Damasio, "Alzheimer's Disease and Related Dementias," *Cecil Textbook of Medicine*, 20th Edition, vol. 2, pp. 1992-1996, (1996).

Dean, [Editor]. "Recent Advances in the Synthesis and Applications of Radiolabeled Development," *Curr., Pharm. Des.*, vol. 6, No. 10, [Table of Contents] CAN 133:68895 AN 2000:473538 CAPLUS; 3 pages, (2000).

Di Chiara, "Drug addiction as dopamine-dependent associative learning disorder," *Eur. J. Pharmacol.*, 375: 13-30, (1999).

Eli Lilly and Company, "Zyprexa Olanzapine Tablets . . ." MedWatch Safety Alerts for Human Medical Products, FDA [online]. Retrieved rom the Internet< URL: http://www.fda.gov/medwatch/safety/2006/Aug_Pls/Zyprexa_Pl.pdf>, 31 pages, (2004).

Evans, "Synthesis of radiolabeled compounds," *J. Radioanal. Chem.*, 64(1-2):9-32, (1981).

Glase et al., "4-bromo-1-methoxy-N-[2-(4-aryl-1-piperazinyl)ethyl)]-2-naphthalenecarboxamides: Selective dopamine D3 receptor partial agonists," *Bioorganic & Medicinal Chemistry Letters*, 6(12):1361-1366, (1996).

Goodwin and Jamison, In: *Manic-depressive illness*, New York: Oxford University Press, pp. 642-647, (1990).

Greengrass and Bremner, "Binding characteristics of 3H-prazosin to rat brain alpha-adrenergic receptors," *Eur. J. Pharmacol.*, 55(3):323-326, (1979).

Guérémy et al., "2-Amino-6-chloro-4-(N-methylpiperazino)pyrimidines, inhibitors of spiroperidol binding," *J. Med. Chem.*, 25(12):1459-1465, (1982).

Gurevich and Joyce, "Distribution of dopamine D3 receptor expressing neurons in the human forebrain: comparison with D2 receptor expressing neurons," *Neuropsychopharmacology*, 1999, 20:60-80.

Gurevich et al., "Mesolimbic dopamine D3 receptors and use of antipsychotics in patients with schizophrenia. A postmortem study." *Arch Gen Psychiatry.*, 54(3):225-232, (1997).

Guy, *ECDEU Assesment Manual for Psychopharmacology.* Rockville, Md: US Department of Health, Education, and Welfare, pp. 218-222, Publication ADM 76-338, (1976).

Gyertyan and Saghy, "Effects of dopamine $D_3$ receptor antagonists on spontaneous and agonist-reduced motor activity in NMRI mice and Wistar rats: comparative study with nafadotride, U 99194A and SB 277011," *Behavioural Pharmacology*, 15(4):253-262, (2004).

Gyertyán and Sághu, "The selective dopamine D3 receptor antagonists, SB 277011-A and S 33084 block haloperidol-induced catalepsy in rats," *Eur. J. Pharmacol.*, 572:171-174, (2007).

Gyertyán et al., "Subnanomolar dopamine D3 receptor antagonism coupled to moderate D2 affinity results in favourable antipsychotic-like activity: Behavioral Data," [abstract]. *Int. J. Neuropsychopharmacol.*, 5 Suppl. 1:174, 2002.

Heidbreder et al., "The role of central dopamine D3 receptors in drug addiction: a review of pharmacological evidence," *Brain Res. Rev.*, 49:77-105, (2005).

Janssen, "Risperdal Consta (risperidone) Long-Acting Injection," MedWatch Safety Alerts for Human Medical Products, FDA [online] Retrieved from the Internet:< URL: http://www.fda.gov/medwatch/safety/2006/Sep_Pls/RisperdalConsta_Pl.pdf>, 39 pages (2006).

Joyce, "Dopamine D3 receptor as a therapeutic target for antipsychotic and antiparkinsonian drugs," *Pharmacol. Therap.*, 90:231-259, (2001).

Kabalka and Varma, "The synthesis of radiolabeled compounds via organometallic intermediates," *Tetrahedron*, 45(21):6601-6621, (1989).

Kay et al., "The positive and negative syndrome scale (PANSS) for schizophrenia," *Schizophr. Bull.*, 13:261-276, (1987).

Keck, "The management of acute mania," *British Medical Journal*, 327(7422):1002-1003, (2003).

King et al. (Oral solid dosage forms, in Remington's Pharmaceutical Sciences; Gennaro, A., Ed., 17th Edition, Mack Publishing Company, Easton PA, Chapter 90, pp. 1603-1632, (1985).

Laszy et al., "Dopamine D3 receptor antagonists improve the learning performance in memory impaired rats," *Psychopharmacol.*, 179(3):567-575, (2005).

Layzer, Degenerative Diseases of the Nervous System, *Cecil Textbook of Medicine*, 20th Edition, vol. 2, pp. 2050-2057, (1996).

Le Foll et al., "Dopamine D3 receptor ligands for the treatment of tobacco dependence," *Expert Opin Investig Drugs*, 16(1):45-57, (2007).

Lehman et al., "Practice guideline for the treatment of patients with schizophrenia, second edition," *Am. J. Psychiatry*, 161(2 Suppl):1-56, (2004).

Levant and McCarson, "D(3) dopamine receptors in rat spinal cord: implications for sensory and motor function," *Neurosci. Lett.*, 303:9-12 (2001).

Levant et al., "Dopamine $D_3$ receptor: relevance for the drug treatment of Parkinson's disease," *CNS Drugs*, 12:391-402, (1999).

Levant, "The D3 dopamine receptor: neurobiology and potential clinical relevance," *Pharmacol. Rev.*, 49(3):231-252, (1997).

Maj et al., "Effect of antidepressant drugs administered repeatedly on the dopamine D3 receptors in the rat brain," *Eur. J. Pharmacol.* 351:31-37, (1998).

Millan et al., "S33084, a novel, potent, selective, and competitive antagonist at dopamine D(3)-receptors: II. Functional and behavioral profile compared with GR218,231 and L741,626," *J. Pharmacol. Exp. Ther.*, 2000, 293:1063-1073.

Millan et al., "The dopamine D3 receptor antagonist, (+)-S 14297, blocks the cataleptic properties of haloperidol in rats," *Eur. J. Pharmacol.*, 321:R7-R9, (1997).

Montgomery and Asberg, "A new depression scale designed to be sensitive to change," *Br. J. Psychiatry*, 134:382-389, (1979).

Mueser and McGurk, "Schizophrenia," *Lancet*, 363:2063-2072, (2004).

Müller-Oerlinghausen et al., "Bipolar disorder," *Lancet*, 359(9302):241-247, (2002).

Nassar et al., "Improving the decision-making process in structural modification of drug candidates: reducing toxicity," *Drug Discov Today*, 9(24):1055-1064, (2004).

Nyberg et al., "Positron emission tomography of in-vivo binding characteristics of atypical antipsychotic drugs. Review of D2 and 5-HT2 receptor occupancy studies and clinical response," *Br. J. Psychiatry. Suppl.*, 29:40-44, (1996).

Pacher and Kecskeméti, "Cardiovascular side effects of new antidepressants and antipsychotics: new drugs, old concerns?" *Curr. Pharm. Des.*, 10(20):2463-2475, (2004).

Papp and Wieronska, "Antidepressant-like activity of amisulpride in two animal models of depression," *J. Psychopharmacol.*, 14:46-52, (2000).

Pilla et al., "Selective inhibition of cocaine-seeking behaviour by a partial dopamine D3 receptor agonist," *Nature*, 400:371-375, (1999).

(56) References Cited

OTHER PUBLICATIONS

Reavill et al., "Pharmacological actions of a novel, high-affinity, and selective human dopamine D(3) receptor antagonist, SB-277011-A," *A. J. Pharmacol. Exp. Ther.*, 294:1154-1165, (2000)
Rogóz et al., "Anxiolytic-like effect of nafadotride and PNU 99194A, dopamine D3 receptor antagonists in animal models," *Pol J Pharmacol.*, 52(6):456-462, (2000).
Russell, "Neurobiology of animal models of attention-deficit hyperactivity disorder," *J. Neurosci. Methods* 161:185-198, (2007).
Sachs, "Unmet clinical needs in bipolar disorder," *J. Clin. Psychopharmacol.*, 23(3 Suppl 1):S2-S8, (2003).
Sautel et al., "Nafadotride, a potent preferential dopamine D3 receptor antagonist, activates locomotion in rodents," *J. Pharmacol. Exp. Ther.*, 1995, 275:1239-1246.
Schwartz et al., "Dopamine D3 receptor: basic and clinical aspects," *Clin. Neuropharmacol.*, 16(4):295-314, (1993)
Schwartz et. al., "Possible implications of the dopamine D(3) receptor in schizophrenia and in antipsychotic drug actions," *Brain Res. Rev.*, 31(2-3):277-287, (2000).
Seeman, "Antipsychotic drugs, dopamine receptors and schizophrenia," *Clin. Neurosci. Res.*, 1:53-60, (2001)
Seeman, "Brain dopamine receptors" *Pharmacological Reviews*, 32(3): 229-313 (1980).
Shafer and Levant, "The D3 dopamine receptor in cellular and organismal function," *Psychopharmacology* (Berl), v, 135:1-16, 1998.
Shalev et al., "Neurobiology of relapse to heroin and cocaine seeking: a review.," *Pharmacol. Rev.* 54 (1), 1-42, (2002).
Sigala et al., "Opposite effects of dopamine $D_2$ and $D_3$ receptors on learning and memory in the rat," *Eur. J. Pharmacol.*, 336:107-112, (1997).
Smith et al., "The dopamine D3/D2 receptor agonist 7-OH-DPAT induces cognitive impairment in the marmoset," *Pharmacol. Biochem. Behav.*, 63:201-211, (1999).
Sokoloff et al., "Molecular cloning and characterization of a novel dopamine receptor (D3) as a target for neuroleptics," *Nature*, 347:146-151, (1990).
Souillac, et al., Characterization of Delivery Systems, Differential Scanning Calorimetry, pp. 217-218 (in Encyclopedia of Controlled Drug Delivery, 1999, John Wiley & Sons, pp. 212-227), (1999).
Stahl and Grady, "A critical review of atypical antipsychotic utilization: comparing monotherapy with polypharmacy and augmentation," *Curr. Med. Chem.*, 11:313-327, (2004).
Stahl, *Essential Psychopharmacology: Neuroscientific Basis and Practical Applications*, 2nd ed., p. 409, Cambridge University Press, pp. 409-414, (2000).
Steiner et al., "D3 dopamine receptor-deficient mouse: evidence for reduced anxiety," *Physiol Behav.*, 63(1):137-141, (1997).
Stemp et al., "Design and synthesis of trans-N-[4-[2-(6-cyano-1,2,3, 4-tetrahydroisoquinolin-2-yl)ethyl]cyclohexyl]-4-quinolinecarboxamide (SB-277011): A potent and selective dopamine D(3) receptor antagonist with high oral bioavailability and CNS penetration in the rat," *J. Med. Chem.*, 43(9):1878-1885, (2000).
Tada et al., "Combined treatment of quetiapine with haloperidol in animal models of antipsychotic effect and extrapyramidal side effects: comparison with risperidone and chlorpromazine," *Psychopharmacology (Berl)*, 176(1):94-100, (2004).
Thanos et al., "The effects of two highly selective dopamine D3 receptor antagonists (SB-277011A and NGB-2904) on food self-administration in a rodent model of obesity," *Pharmacol Biochem Behav.* 89: 499-507, (2008).
Ukai et al., "Effects of the dopamine D3 receptor agonist, R(+)-7-hydroxy-N,N-di-n-propyl-2-aminotetralin, on memory processes in mice," *Eur. J. Pharmacol.*, 324:147-151, (1997).
Ulrich, Chapter 4: Crystallization, *Kirk-Othmer Encyclopedia of Chemical Technology*, 7 pages, (2002).
van der Kooij and Glennon, "Animal models concerning the role of dopamine in attention-deficit hyperactivity disorder," *Neuroscience and Biobehavioral Reviews*, 31: 597-618, (2007).
Waters et al., "Differential effects of dopamine D2 and D3 receptor antagonists in regard to dopamine release, in vivo receptor displacement and behavior," *J. Neural. Transm. Gen. Sect.*, 98:39-55, (1994)
West, *Solid State Chemistry and Its Applications*, Wiley, pp. 358, (1988).
Willner et al., "Dopaminergic mechanism of antidepressant action in depressed patients," *J. Affective Disorders* 86: 37-45, (2005).
Wong and Van Tol, "Schizophrenia: from phenomenology to neurobiology," *Neurosci. Biobehav. Rev.*, 27(3):269-306, (2003)
World Health Organization, World Health Report 2001, "Mental Health: New Understanding, New Hope." http://www.who.int/whr/2001/en/2001, (2001).
Wyatt and Henter, "An economic evaluation of manic-depressive illness—1991," *Soc. Psychiatry Psychiatr. Epidemiol.*, 30(5):213-219, (1995).
Youdim, "The path from anti Parkinson drug selegiline and rasagiline to multifunctional neuroprotective anti Alzheimer drugs ladostigil and m30," *Curr Alzheimer Res.*, 3(5):541-550, 2006.
Young, et al., "A rating scale for mania: reliability, validity and sensitivity," *The British Journal of Psychiatry*, 133:429-435, (1978)
Zink et al., "Combination of amisulpride and olanzapine in treatment-resistant schizophrenic psychoses," *Eur. Psychiatry*, 19:56-58, (2004).
International Search Report for PCT/HU2009/000109, mailed Mar. 11, 2010, 2 pages.
International Preliminary Report on Patentability and Written Opinion, issued Jun. 21, 2011, 6 pages.
Morissette et al; High-throughput crystallization: polymorphs, salts, co-crystals and solvates of pharmaceutical solids; Adv Drug Deliv Rev; Feb. 2004; 56(3):275-300.
Nassar et al; Improving the decision-making process in structural modification of drug candidates: reducing toxicity; Drug Discov Today; Dec. 2004; 9(24):1055-1064.
Nassar et al; Improving the decision-making process in the structural modification of drug candidates: enhancing metabolic stability; Drug Discov Today; Dec. 2004; 9(23):1020-1028.
Pacher and Kecskeméti; Cardiovascular side effects of new antidepressants and antipsychotics: new drugs, old concerns?; Curr. Pharm. Des.; 2004; 10(20):2463-2475.

PROCESS FOR THE PREPARATION OF PIPERAZINE COMPOUNDS AND HYDROCHLORIDE SALTS THEREOF

CROSS-REFERENCE TO RELATED APPLICATIONS

This application is a National Stage application under 35 U.S.C. §371 of International Application No. PCT/HU2009/000109, having an International Filing Date of Dec. 18, 2009, which claims the benefit of priority of HU Application No. P0800765, having a filing date of Dec. 18, 2008, all of which are incorporated herein in their entirety.

TECHNICAL FIELD

The invention relates to a new process for the preparation of trans N-{4-{2-[4-(2,3-dichlorophenyl)-piperazine-1-yl]-ethyl}-cyclohexyl}-carbamide compounds of general formula (I)

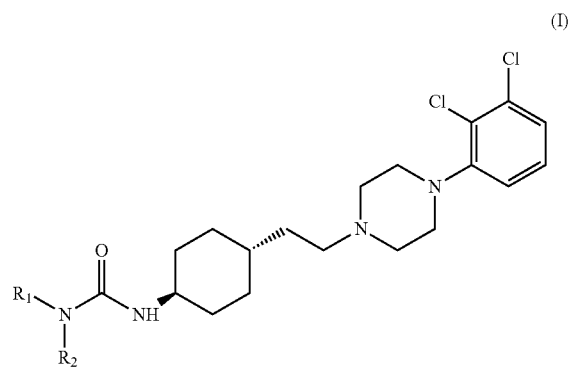

(I)

wherein $R_1$ and $R_2$ represent independently
  hydrogen or
  $C_{1-6}$ alkyl with straight or branched chain optionally substituted with aryl group, or
  $R_1$ and $R_2$ together with the adjacent nitrogen atom may form an optionally substituted, saturated or unsaturated, monocyclic or bicyclic heterocyclic ring which may contain further heteroatoms selected from oxygen, nitrogen or sulphur atoms
  $C_{2-7}$ alkenyl containing 1-3 double bonds, or
  monocyclic, bicyclic or tricyclic aril group optionally substituted with one or more $C_{1-6}$-alkoxy, trifluoro-$C_{1-6}$-alkoxy, $C_{1-6}$ alkoxycarbonyl, $C_{1-6}$ alkanoyl, aryl, $C_{1-6}$ alkylthio, cyano groups or halogen atom
  optionally substituted monocyclic, bicyclic, or tricyclic $C_{3-14}$ cycloalkyl group and hydrochloride salts and/or hydrates and/or solvates thereof.

DESCRIPTION OF THE PRIOR ART

The base form of the compounds of general formula (I) was originally disclosed in the Hungarian Patent Specification No. P0302451. In the specification three reaction routes (A, B, C methods) are given for the preparation of the base form of compounds of formula (I). In the method "A" a suitable amine is reacted with a (thio)carbamoylchloride to give the end products of general formula (I). According to the A Method of P0302451 the "A" procedure gives the product with a yield of only 65% and with very long reaction time. According to Method B an iso(thio)cyanate is reacted with an amine compound. Drawback of the "B" process is that using this procedure only the compound of general formula (I) may be prepared wherein one of the $R_1$ and $R_2$ groups represents hydrogen. According to the "C" Method of P0302451 a suitable amine is transformed to an iso(thio)cyanate derivative then this iso(thio)cyanate derivative is reacted with an amine to give the desired end products of formula (I). The total yield of Method C is very low, only 52%.

Drawbacks of the "A" and "C" procedures are the long reaction times (48 and 20 hours) and poor yields (65% and 52%). Besides, in the "A" and "C" procedures the end product obtained should be purified in an additional purification (re-crystallization) step to give the product in suitable quality.

BRIEF DESCRIPTION OF THE INVENTION

Our aim was to develop a process which provides both unsubstituted and mono- and disubstituted carbamide compounds of general formula (I) with excellent yield.

We have surprisingly found that by reacting trans 4-{2-[4-(2,3-dichlorophenyl)-piperazine-1-yl]-ethyl}-cyclohexylamine of formula (III)

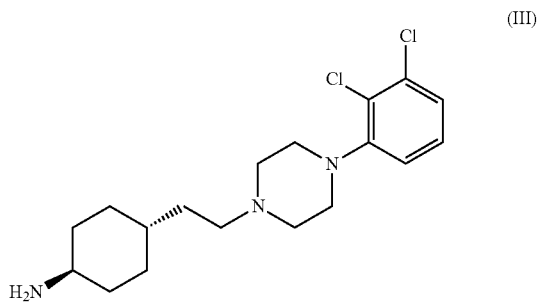 [SMILES: N[C@H]1CC[C@H](CCN2CCN(c3cccc(Cl)c3Cl)CC2)CC1]

(III)

or a salt and/or a hydrate and/or a solvate thereof with a carbonic acid derivative of general formula (VI)

R—O—CO—Z         (VI)

wherein R is $C_{1-6}$ straight or branched alkyl or fully halogenated $C_{1-2}$ alkyl, Z is —O—R or —X, wherein R is as described above, X is halogen, then reacting the compound of general formula (IV) obtained

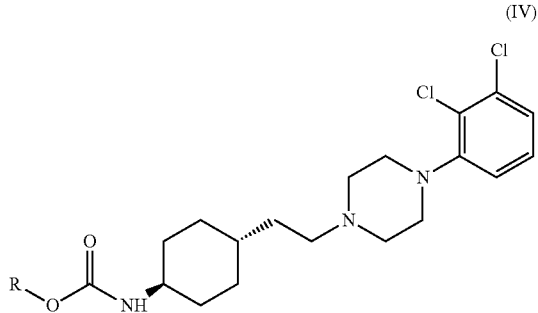

(IV)

wherein R is as described above, with an amine derivative of general formula (V)

(V)

wherein
R₁ and R₂ represent independently
  hydrogen or
  $C_{1-6}$ alkyl with straight or branched chain optionally substituted with aryl group, or
  $C_{2-7}$ alkenyl containing 1-3 double bonds, or
  monocyclic, bicyclic or tricyclic aryl optionally substituted with one or more $C_{1-6}$ alkoxy, trifluoro-$C_{1-6}$ alkoxy, $C_{1-6}$ alkoxycarbonyl, $C_{1-6}$ alcanoyl, aryl, $C_{1-6}$ alkyltio, halogen, or cyano groups, or
  optionally substituted monocyclic, bicyclic or tricyclic $C_{3-14}$ cycloalkyl group, or
  R₁ and R₂ together with the adjacent nitrogen may form a saturated or unsaturated optionally substituted monocyclic or bicyclic heterocyclic ring which may contain further heteroatoms, selected from oxygen, nitrogen or sulphur atoms
we get the compounds of general formula (I)

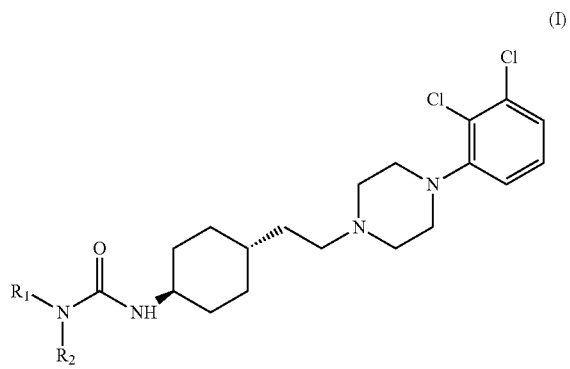
(I)

wherein R₁ and R₂ are as described above with very high yield.

DETAILED DESCRIPTION OF THE INVENTION

The invention relates to a new process for the preparation of compounds of general formula (I)

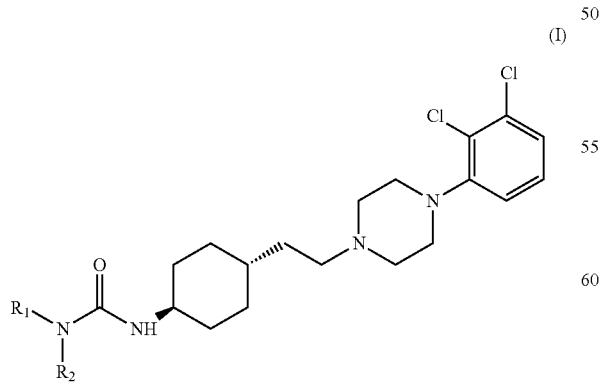
(I)

wherein R₁ and R₂ represent independently
  hydrogen or
  $C_{1-6}$ alkyl with straight or branched chain optionally substituted with aryl group, or
  $C_{2-7}$ alkenyl containing 1-3 double bonds, or
  monocyclic, bicyclic or tricyclic aryl group optionally substituted with one or more $C_{1-6}$ alkoxy, trifluoro-$C_{1-6}$ alkoxy, $C_{1-6}$ alkoxycarbonyl, $C_{1-6}$ alcanoyl, aryl, $C_{1-6}$ alkyltio, halogen, or cyano groups, or
  optionally substituted monocyclic, bicyclic or tricyclic $C_{3-14}$ cycloalkyl group, or
  R₁ and R₂ together with the adjacent nitrogen may form a saturated or unsaturated optionally substituted monocyclic or bicyclic heterocyclic ring which may contain further heteroatoms selected from oxygen, nitrogen or sulphur atoms
and hydrochloride salts, and/or hydrates and/or solvates thereof.

In the meanings of R₁ and R₂ the aryl group represents for example phenyl, tolyl, naphthyl or phenanthryl groups.

Performing the process according to the invention the trans 4-{2-[4-(2,3-dichlorophenyl)-piperazine-1-yl]-ethyl}-cyclohexyl-amine compound of formula (III)

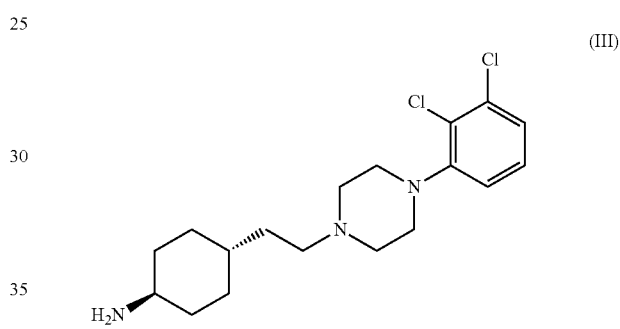
(III)

or a salt or a hydrate or a solvate thereof is dissolved or suspended in an inert solvent in the presence of a base and reacted with a carbonic acid derivative of general formula (VI)

R—O—CO—Z (VI)

wherein R is $C_{1-6}$ alkyl with straight or branched chain or $C_{1-2}$ fully halogenated alkyl, Z is —O—R or —X, wherein R is as described above, X is halogen to give a compound of general formula (IV)

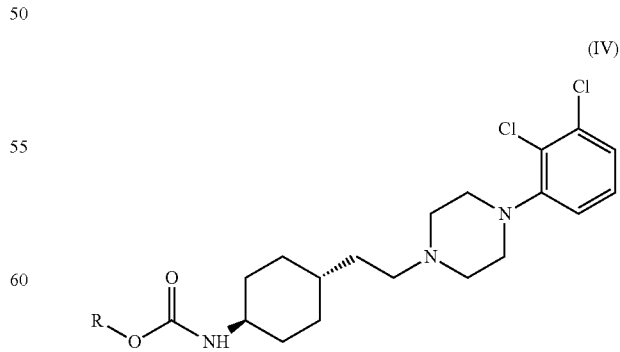
(IV)

wherein R is $C_{1-6}$ alkyl or fully halogenated $C_{1-2}$ alkyl group. Then the compound of general formula (IV) obtained is reacted with an amine of general formula (V)

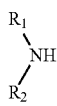

wherein $R_1$ and $R_2$ are as described above to give a compound of general formula (I). The above reaction may be carried out in situ in an inert solvent or after the isolation of the compound of general formula (IV).

Suitable solvents, which can be used in the process according to the invention include inert, water immiscible solvents, for example toluene, dichloromethane, chlorobenzene or xylene. In a preferred embodiment of the invention the solvent is dichloromethane.

Suitable bases, which can be used in the process according to the invention include organic bases, preferably tertiary amines, for example triethylamine.

In the substituents meanings of the carbonic acid derivatives of general formula (VI) when R represents fully halogenated alkyl group, the alkyl group may be for example trichloromethyl or pentachloroethyl group. In a preferred embodiment of the invention the carbonic acid derivative is chloroformic acid ester or bis-trichloromethylcarbonate.

Performing the process according to the invention the reaction between the compounds of general formula (IV) and (V) may be carried out in such a manner, that after an isolation step the urethane compound of general formula (IV) is reacted with an amine of general formula (V). However, owing to the bad isolability of compounds of general formula (IV) the above reaction is preferably may be performed in situ in an inert solvent in such a way that an appropriate amine of general formula (V) is added to the reaction mixture of formulas of (III) and (VI). In this latter case, starting from the compound of formula (III) via the non-isolated compound of general formula (IV) we get the compound of general formula (I) in high yield of over 90%.

In the light of the technical literature the advantages of the process according to the invention are as follows: the yield increases from 52-65% to 95%, and by using the procedure besides the N-monosubstituted compounds of formula (I) N-disubstituted compounds can be obtained too.

The invention relates to a process for the preparation the trans N-{4-{2-[4-(2,3-dichlorophenyl)-piperazine-1-yl]ethyl}-cyclohexyl}-carbamide base of general formula (I) and the hydrochloride salts thereof.

In an embodiment of the invention to give the trans N-{4-{2-[4-(2,3-dichlorophenyl)-piperazine-1-yl]ethyl}-cyclohexyl}-carbamide base of general formula (I) work-up of the reaction mixture is carried out in such a manner that after an aqueous dilution the reaction mixture is extracted with an organic solvent and the base compound of formula (I) may be isolated by a known manner preferably by removing the solvent.

In a preferred embodiment of the invention the base is not isolated but after an aqueous dilution the reaction mixture is acidified with hydrochloric acid to pH 2-4, then the reaction mixture is converted to an aqueous suspension by distillation and the hydrochloride salt of the compound of general formula (I) is isolated in high purity ad yield of over 90%.

EXAMPLES

The invention is illustrated by the following non-limiting examples.

Example 1

Trans N-(4-{2-[4-(2,3-dichlorophenyl)-piperazine-1-yl]-ethyl}-cyclohexyl)-carbamic acid methylester 6.45 g (0.015 mol) of dihydrochloride of compound of formula (III) was added to a mixture of 125 ml dichloromethane and 12.25 ml triethylamine and the thick suspension obtained was stirred at a temperature between 20-25° C. for one hour. The so obtained suspension was added to a solution of 2.3 ml (0.03 mol) methyl chloroformate in 25 ml of dichloromethane at a temperature between 5-10° C. The reaction mixture obtained was stirred at a temperature between 20-25° C. for 3 hours then extracted with 3×150 ml (150 g) of distilled water. The organic phase was evaporated in vacuum and the residue was recrystallized from methanol. In this manner 4.5 g of the title product was obtained.
Yield: 72%.
Melting point: 143-147° C.

Example 2

Trans N-(4-{2-[4-(2,3-dichlorophenyl)-piperazine-1-yl]-ethyl}-cyclohexyl)-carbamic acid isopropylester 6.45 g (0.015 mol) of dihydrochloride of compound of formula (III) was added to a mixture of 125 ml dichloromethane and 12.25 ml of triethylamine and the thick suspension obtained was stirred at a temperature between 20-25° C.-on for one hour. The suspension was added to a solution of 3.7 g (0.03 mol) of isopropyl chloroformate in 30 ml of toluene at a temperature between 5-10° C. The reaction mixture was stirred at a temperature between 20-25° C. for 3 hours and then extracted with 3×150 ml (150 g) of distilled water. The organic phase was evaporated in vacuum and the residue obtained was recrystallized from isopropanole.
In this manner 4.4 g of title compound was obtained.
Yield: 67%.
Melting point: 128-131° C.

Example 3

Trans 4-{2-[4-(2,3-dichlorophenyl)-piperazine-1-yl]-ethyl}-N,N-dimethylcarbamoyl-cyclohexylamine 6.45 g (0.015 mol) of dihydrochloride of compound of formula (III) was added to a mixture of 125 ml of dichloromethane and 12.25 ml of triethylamine and the thick suspension obtained was stirred at a temperature between 20-25° C. for one hour. The suspension was added to a solution of 4.9 g of bis(trichloromethyl)carbonate in 50 ml of dichloromethane at a temperature between −5-(−10)° C. for one hour. The reaction mixture obtained was added to a solution of 13 g dimethylamine in 100 ml isopropyl alcohol (IPA) (40 ml, 0.12 mol) cooled at a temperature between 0-(−10)° C. during which the temperature of the reaction mixture was kept under 0° C. After stirring at a temperature between 0-(−5)° C. for 30 minutes to the reaction mixture 100 ml of distilled water was added under stirring. Then the pH of the aqueous phase was adjusted to 7-8 by adding concentrated hydrochloric acid and volume of the reaction mixture was concentrated to 130 ml under vacuum. To the reaction mixture obtained additional 70 ml of distilled water was added and the mixture was concentrated to 170 ml under vacuum. The suspension was stirred at 20-25° C. for one hour and the product obtained was isolated by filtration.

In this manner 6.6 g of title compound was obtained.
Yield: 95%
Melting point: 208-211° C.

Example 4

Trans 4-{2-[4-(2,3-dichlorophenyl)-piperazine-1-yl]-ethyl}-N,N-dimethylcarbamoyl-cyclohexylamine hydrochloride 6.45 g (0.015 mol) dihydrochloride of formula (III) was added to a mixture of 125 ml of dichloromethane and 12.25 ml of triethylamine and the thick suspension obtained was stirred at a temperature between 20-25° C. for one hour. The suspension was added to the solution of 4.9 g of bis(trichloromethyl)carbonate in 50 ml of dichloromethane at a temperature between −5-(−10)° C. for one hour. The reaction mixture obtained was added to a solution of 13 g dimethylamine in 100 ml isopropyl alcohol (IPA) (40 ml, 0.12 mol) cooled at a temperature between 0-(−10)° C. during which the temperature of the reaction mixture was kept under 0° C. After stirring at a temperature between 0-(−5)° C. for 30 minutes 100 ml of distilled water was added to the reaction mixture under stirring. Then the pH of the aqueous phase is adjusted to 2-3 by adding concentrated hydrochloric acid and the reaction mixture was concentrated to 130 ml, additional 70 ml of distilled water was added and the mixture was concentrated to 170 ml. The suspension was stirred at 20-25° C. for one hour and the product obtained was isolated by filtration.

In this manner 6.7 g of title compound was obtained.
Yield: 96%
Melting point: 221-224° C.

Example 5

Trans 4-{2-[4-(2,3-dichlorophenyl)-piperazine-1-yl]-ethyl}-N,N-dimethylcarbamoil-cyclohexylamine hydrochloride 6.72 g (0.015 mol) dihydrochloride monohydrate of compound of formula (III) was added to a mixture of 125 ml of dichloromethane and 12.25 ml of triethylamine and the thick suspension obtained was stirred at a temperature between 20-25° C. for one hour. The suspension was added to the solution of 4.9 g of bis(trichloromethyl)carbonate in 50 ml of dichloromethane at a temperature between −5-(−10)° C. for one hour. The reaction mixture obtained was added to a solution of 13 g dimethylamine in 100 ml isopropyl alcohol (IPA) (40 ml, 0.12 mol) cooled at a temperature between 0-(−10)° C. during which the temperature of the reaction mixture was kept under 0° C. After stirring at a temperature between 0-(−5)° C. for 30 minutes to the reaction mixture 100 ml of distilled water was added and the pH of the aqueous phase was adjusted to 2-3 by adding concentrated hydrochloric acid. The reaction mixture was concentrated to 130 ml under vacuum then additional 70 ml of water was added and the mixture was concentrated to 170 ml. The suspension was stirred at a temperature between 20-25° C. for one hour and the product obtained was isolated by filtration.

In this manner 6.7 g of title compound was obtained.
Yield: 96%.
Melting point: 221-224° C.

Example 6

1-Trans {4-[2-[4-(2,3-dichlorophenyl)-piperazine-1-yl]ethyl]-cyclohexyl}carbamide 6.45 g (0.015 mol) dihydrochloride of compound of formula (III) was added to a mixture of 160 ml of dichloromethane and 12.8 ml of triethylamine and the thick suspension obtained was stirred at a temperature between 20-25° C. for one hour. The suspension was added to the solution of 4.9 g of bis(trichloromethyl)carbonate in 75 ml of dichloromethane at a temperature between −5-(−10)° C. for one hour. The reaction mixture obtained was added to a solution of ammonia in methanol (110 ml, 17 g/100 ml) cooled at a temperature between 0-(−10)° C. during which the temperature of the reaction mixture was kept under 0° C. After stirring at a temperature between 0-(−5)° C. for 30 minutes the reaction mixture was concentrated to 100 ml in vacuum then 800 ml of distilled water was added. The suspension was stirred at 20-25° C. for one hour and the product obtained was isolated by filtration.

In this manner 5.6 g of title compound was obtained.
Yield: 94%.
Melting point: 221-224° C.

Example 7

Trans N-{4-{2-[4-(2,3-dichlorophenyl)-piperazine-1-yl]ethyl}-cyclohexyl}-N'-methylcarbamide hydrochloride 6.45 g (0.015 mol) dihydrochloride of compound of formula (III) was added to a mixture of 125 ml of dichloromethane and 12.25 ml of triethylamine and the thick suspension obtained was stirred at a temperature between 20-25° C. for one hour. The suspension was added to the solution of 4.9 g of bis(trichloromethyl)carbonate in 50 ml of dichloromethane at a temperature between −5-(−10)° C. for one hour. The reaction mixture obtained was added to a solution of methylamine in isopropyl alcohol (IPA) (60 ml, 12.5 g/100 ml) cooled at a temperature between 0-(−10)° C. during which the temperature of the reaction mixture was kept under 0° C. After stirring at a temperature between 0-(−5)° C. for 30 minutes to the reaction mixture 130 ml of distilled water was added then the pH of the aqueous phase was adjusted to 2-3 by adding concentrated hydrochloric acid. The reaction mixture was concentrated to 120 ml in vacuum and additional 70 ml of distilled water was added. The suspension was stirred at a temperature between 20-25° C. for one hour and the product obtained was isolated by filtration.

In this manner 6.6 g of title compound was obtained.
Yield: 95%.
Melting point: 230-255° C.

Example 8

Trans N-{4-{2-[4-(2,3-dichlorophenyl)-piperazine-1-yl]-ethyl}-cyclohexylcarbamide hydrochloride 6.45 g (0.015 mol) dihydrochloride of compound of formula (III) was added to a mixture of 160 ml of dichloromethane and 12.8 ml of triethylamine and the thick suspension obtained was stirred at a temperature between 20-25° C. for one hour. The suspension was added to a solution of 4.9 g of bis(trichloromethyl)carbonate in 75 ml of dichloromethane at a temperature between −5-(−10)° C. for one hour. The reaction mixture obtained was added to a solution of ammonia in methanol (110 ml, 17 g/100 ml) cooled at a temperature between 0-(–10)° C. during which the temperature of the reaction mixture was kept under 0° C. After stirring at 0-10° C. for 30 minutes the reaction mixture was concentrated to 20 ml in vacuum then 140 ml of distilled water was added. The pH of the aqueous phase was adjusted to 2-3 by adding concentrated hydrochloric acid. The suspension was stirred at a temperature between 20-25° C. for one hour and the product obtained was isolated by filtration. In this manner 5.86 g of title compound was obtained.
Yield: 90%.
Melting point: 250-253° C. (decomp.).

Example 9

Trans N-{4-{2-[4-(2,3-dichlorophenyl)-piperazine-1-yl]-ethyl}-cyclohexyl}-morpholine-4-carbonic amide 6.45 g (0.015 mol) dihydrochloride of compound of formula (III) was added to a mixture of 125 ml of dichloromethane and 12.25 ml of triethylamine and the thick suspension obtained was stirred at a temperature between 20-25° C. for one hour. The suspension was added to a solution of 4.9 g of bis(trichloromethyl)carbonate in 50 ml of dichloromethane at a temperature between –5-(–10)° C. for one hour. The so obtained reaction mixture was added to the solution of 10.44 g (0.12 mol) morpholine in 70 ml of isopropyl alcohol (IPA) cooled at a temperature between 0-(–10)° C. during which the temperature of the reaction mixture was kept under 0° C. After stirring at 0-10° C. for 30 minutes to the reaction mixture 100 ml of distilled water was added under stirring and the pH of the aqueous phase was adjusted to 7-8 by adding concentrated hydrochloric acid. The reaction mixture was concentrated to 130 ml under vacuum and additional 100 ml of distilled water was added. Volume of the reaction mixture was decreased to 150 ml in vacuum. The suspension was stirred at a temperature between 20-25° C. for one hour and the product obtained was isolated by filtration.
In this manner 6.55 g of title compound was obtained.
Yield: 93%.
Melting point: 204-206° C. (decomp).

Example 10

Trans N-{4-{2-[4-(2,3-dichlorophenyl)-piperazine-1-yl]-ethyl}-cyclohexyl}-morpholine-4-carbonic amide hydrochloride 6.45 g (0.015 mol) dihydrochloride of compound of formula (III) was added to a mixture of 125 ml dichloromethane and 12.25 ml of triethylamine and the thick suspension obtained was stirred at a temperature between 20-25° C. for one hour. The suspension was added to a solution of 4.9 g of bis(trichloromethyl)carbonate in 50 ml of dichloromethane at a temperature between –5-(–10)° C. for one hour. The reaction mixture obtained was added to a solution of 10.44 g of (0.12 mol) morpholine in 70 ml of isopropyl alcohol (IPA) cooled to a temperature between 0-(–10)° C. during which the temperature of the reaction mixture was kept under 0° C. After stirring at 0-10° C. for 30 minutes to the reaction mixture 100 ml of distilled water was added under stirring then the pH of the aqueous phase was adjusted to 2-3. The reaction mixture was concentrated to 130 ml under vacuum and further 100 ml of distilled water was added. Then the volume of the reaction mixture was decreased to 150 ml under vacuum. The suspension was stirred at a temperature between 20-25° C. for one hour and the product obtained was isolated by filtration.
In this manner 7.1 g of title product was obtained.
Yield: 94%.
Melting point: 197° C. (decomp.).

The invention claimed is:
1. Process for the preparation of compounds of general formula (I)

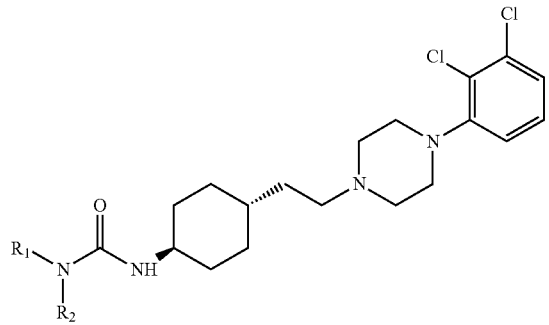

(I)

wherein $R_1$ and $R_2$ represent independently
hydrogen or
$C_{1-6}$ alkyl with straight or branched chain optionally substituted with aryl group, or
$C_{2-7}$ alkenyl containing 1-3 double bonds, or
monocyclic, bicyclic or tricyclic aryl optionally substituted with one or more C1-6 alkoxy, trifluoro-$C_{1-6}$ alkoxy, $C_{1-6}$-alkoxycarbonil, $C_{1-6}$alkanoyl, aryl, $C_{1-6}$ alkylthio, halogen or cyano, or
a monocyclic, bicyclic or tricyclic $C_{3-14}$ cycloalkyl group,
$R_1$ and $R_2$ together with the adjacent nitrogen form a saturated or unsaturated monocyclic or bicyclic heterocyclic ring which may contain further heteroatoms selected from oxygen, nitrogen, or sulphur atoms,
and hydrochloric acid salts thereof comprising dissolving or suspending trans 4-{2-[4-(2,3-dichlorophenyl)-piperazine-1-il]-ethyl}-cyclohexylamine of formula (III)

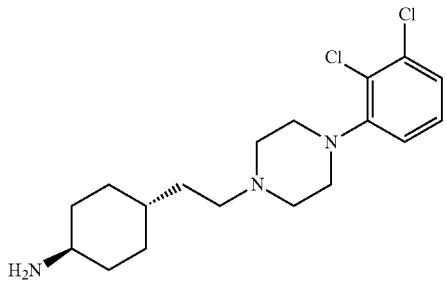

(III)

or a salt or a hydrate or a solvate thereof in an inert solvent in the presence a base then adding a carbonic acid derivative of general formula (VI)

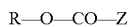

R—O—CO—Z (VI)

wherein R is alkyl with $C_{1-6}$ straight or branched chain or $C_{1-2}$ fully halogenated alkyl, Z is —O—R or —X, wherein R is as described above, X is halogen, and
reacting the compound of general formula (IV) obtained

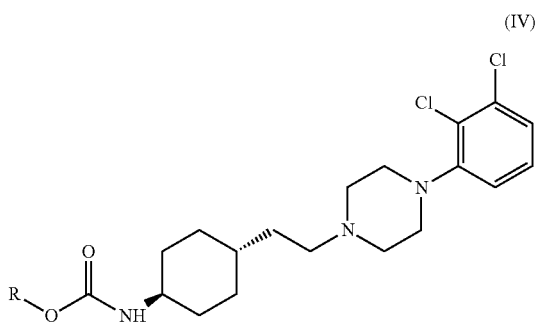

wherein R is as described above,
in situ or, optionally in isolated state with an amine of general formula (V)

wherein $R_1$ and $R_2$ are as described above to obtain the compound of general formula (I) and then optionally forming the hydrochloride salts thereof.

2. The process according to claim 1 wherein the carbonic acid derivative of general formula (VI) is a chloroformate ester or bis(trichloromethyl)carbonate.

3. The process according to claim 1 wherein the reaction of compounds of general formula (IV) and (V) is carried out in situ without isolation of the compound of general formula (IV).

* * * * *

UNITED STATES PATENT AND TRADEMARK OFFICE
CERTIFICATE OF CORRECTION

PATENT NO. : 8,569,498 B2
APPLICATION NO. : 13/140281
DATED : October 29, 2013
INVENTOR(S) : Laszlo Czibula et al.

It is certified that error appears in the above-identified patent and that said Letters Patent is hereby corrected as shown below:

On the title page

Item (57), Abstract, Column 2, line 18, please delete "alts" and insert -- salts --, therefor;

Page 2, Column 1 under item (56), (Other Publications), line 27, please delete "Development,"" and insert -- Compounds for Drug Discovery and Development," --, therefor;

Page 2, Column 1 under item (56), (Other Publications), line 34, please delete "rom the" and insert -- from the --, therefor;

Page 2, Column 1 under item (56), (Other Publications), line 56, please delete "Assesment" and insert -- Assessment --, therefor;

Page 3, Column 1 under item (56), (Other Publications), line 6, please delete "456-462," and insert -- 459-462, --, therefor;

In the Claims

Column 10, line 33 (Claim 1), please delete "C1-6 alkoxy" and insert -- $C_{1-6}$ alkoxy --, therefor;

Column 10, line 34 (Claim 1), please delete "$C_{1-6}$-alkoxycarbonil" and insert -- $C_{1-6}$ alkoxycarbonyl --, therefor;

Column 10, line 43 (Claim 1), please delete "1-il]-ethyl}-cyclohexylamine" and insert -- 1-yl]-ethyl}-cyclohexylamine --, therefor; and Column 12, line 1 (Claim 1), please delete "  " and insert -- (V) --, therefor.

Signed and Sealed this
Twelfth Day of August, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,569,498 B2 | Page 1 of 1 |
| APPLICATION NO. | : 13/140281 | |
| DATED | : October 29, 2013 | |
| INVENTOR(S) | : Czibula et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 211 days.

Signed and Sealed this
Fourteenth Day of April, 2015

Michelle K. Lee
*Director of the United States Patent and Trademark Office*